US011116668B1

(12) United States Patent
Haring

(10) Patent No.: US 11,116,668 B1
(45) Date of Patent: Sep. 14, 2021

(54) CROSS-FLANGE TYMPANOSTOMY TUBE

(71) Applicant: Roger D. Haring, Santa Clarita, CA (US)

(72) Inventor: Roger D. Haring, Santa Clarita, CA (US)

(*) Notice: Subject to any disclaimer, the term of this patent is extended or adjusted under 35 U.S.C. 154(b) by 0 days.

(21) Appl. No.: 17/219,750

(22) Filed: Mar. 31, 2021

Related U.S. Application Data

(60) Provisional application No. 63/019,506, filed on May 4, 2020.

(51) Int. Cl.
A61F 11/00 (2006.01)

(52) U.S. Cl.
CPC ..... A61F 11/002 (2013.01); A61F 2230/0069 (2013.01)

(58) Field of Classification Search
CPC .............................. A61M 27/002; A61F 11/002
USPC .................................................. D24/155, 173
See application file for complete search history.

(56) References Cited

U.S. PATENT DOCUMENTS

| 3,871,380 | A | * | 3/1975 | Heros | A61F 11/002 604/264 |
| 4,037,604 | A | * | 7/1977 | Newkirk | A61F 9/00781 604/9 |
| 4,094,303 | A | * | 6/1978 | Johnston | A61F 11/002 128/867 |
| 4,650,488 | A | * | 3/1987 | Bays | A61F 11/002 128/899 |
| 5,178,623 | A | * | 1/1993 | Cinberg | A61F 11/002 606/1 |
| 5,746,725 | A | * | 5/1998 | Shalon | A61F 11/002 604/207 |
| 6,689,302 | B2 | | 2/2004 | Reisdorf | |
| 7,520,897 | B2 | * | 4/2009 | Seder | A61F 2/203 424/404 |
| 8,147,545 | B2 | * | 4/2012 | Avior | A61F 11/002 623/10 |
| 8,197,433 | B2 | * | 6/2012 | Cohen | A61F 11/002 604/8 |

(Continued)

FOREIGN PATENT DOCUMENTS

| CA | 2890730 C | 12/2019 |
| EP | 2649972 B1 | 12/2017 |

OTHER PUBLICATIONS

Wang MC, Wang YP, Chu CH, Tu TY, Shiao AS, Chou P. The protective effect of adenoidectomy on pediatric tympanostomy tube re-insertions: a population-based birth cohort study. PLoS One. Jul. 1, 2014;9(7):e101175. doi: 10.1371/journal.pone.0101175. PMID: 24983459; PMCID: PMC4077749; 2 pages.

(Continued)

Primary Examiner — Ryan J. Severson
(74) Attorney, Agent, or Firm — Cislo & Thomas, LLP

(57) ABSTRACT

The invention provides a pressure equalization or tympanostomy tube for draining and ventilating the middle ear. The tube comprises a short cylindrical body having a first planer extension or flange and a second planer extension or flange. The first flange being equipped with segments which may be trimmed to size to allow for in-theater sizing by a surgeon. In one embodiment, the tube includes a cylindrical bore and in another embodiment, the tube includes a square bore which includes a flap valve for regulating pressure in a patient's middle ear.

18 Claims, 10 Drawing Sheets

(56) References Cited

U.S. PATENT DOCUMENTS

| | | | | |
|---|---|---|---|---|
| 8,317,861 | B2* | 11/2012 | Goldberg | A61L 27/54 623/9 |
| 8,480,610 | B1* | 7/2013 | Hill | A61F 11/002 604/8 |
| 8,579,973 | B2* | 11/2013 | Avior | A61F 11/002 623/10 |
| D707,822 | S* | 6/2014 | Clopp | A61F 11/002 D24/155 |
| 9,011,363 | B2* | 4/2015 | Clopp | A61M 27/002 604/8 |
| 9,023,059 | B2* | 5/2015 | Loushin | A61M 31/00 606/109 |
| 9,370,448 | B2* | 6/2016 | Loushin | A61F 11/002 |
| 10,130,515 | B2 | 11/2018 | Kaplan | |
| 2002/0193879 | A1* | 12/2002 | Seder | A61F 2/203 623/9 |
| 2008/0058831 | A1* | 3/2008 | Fujiwara | A61F 11/002 606/109 |
| 2008/0058832 | A1* | 3/2008 | Fujiwara | A61F 11/002 606/109 |
| 2008/0294255 | A1* | 11/2008 | Gonzales | A61M 27/002 623/10 |
| 2009/0088677 | A1* | 4/2009 | Cohen | A61F 11/002 604/8 |
| 2010/0174366 | A1* | 7/2010 | Avior | A61F 11/002 623/10 |
| 2011/0152875 | A1* | 6/2011 | Gonzales | A61M 27/002 606/108 |
| 2012/0191030 | A1* | 7/2012 | Avior | A61F 11/002 604/9 |
| 2013/0338678 | A1* | 12/2013 | Loushin | A61F 11/002 606/109 |
| 2014/0094733 | A1* | 4/2014 | Clopp | A61M 27/002 604/8 |
| 2016/0262937 | A1 | 9/2016 | Fritsch | |
| 2017/0281230 | A1 | 10/2017 | Andreas | |

OTHER PUBLICATIONS

Hong P, Chadha NK. Tympanostomy tube care for the pediatrician. Clin Pediatr (Phila). Oct. 2013;52(10):899-909. doi: 10.1177/0009922813480884. Epub Mar. 14, 2013. PMID: 23493765; 11 pages.

Yaman H, Guclu E, Yilmaz S, Ozturk O. Myringosclerosis after tympanostomy tube insertion: relation with tube retention time and gender. Auris Nasus Larynx. Dec. 2010;37(6):676-9. doi: 10.1016/j.anl.2010.02.007. Epub Apr. 14, 2010. PMID: 20392579; 2 pages.

Vlastos IM, Houlakis M, Kandiloros D, Manolopoulos L, Ferekidis E, Yiotakis I. Adenoidectomy plus tympanostomy tube insertion versus adenoidectomy plus myringotomy in children with obstructive sleep apnoea syndrome. J Laryngol Otol. Mar. 2011;125(3):274-8. doi: 10.1017/S0022215110002549. Epub Dec. 16, 2010. PMID: 21205368; 2 pages.

* cited by examiner

CROSS-FLANGE TYMPANOSTOMY TUBE

CROSS-REFERENCES TO RELATED APPLICATION

This application claims the benefit of benefit of U.S. Provisional Application Ser. No. 63/019,506, filed on May 4, 2020 and entitled "Tympanostomy Tube," which is incorporated in its entirety herein by this reference.

BACKGROUND OF THE INVENTION

Field of the Invention

The present invention relates to tympanostomy or pressure equalization tubes for ventilating the middle ear cavity and/or draining fluid through the eardrum, and, in particular, to an improved ear tube having a short cylinder length, a surgeon configurable flange, and a valve suitable for regulating the pressure differential between a patient's inner and outer ear.

Background of the Invention

A majority of children may experience at least one episode of otitis media, commonly referred to as an earache, during childhood. The condition is one of the most common diagnoses made by pediatricians. Otitis media is believed to be caused by eustachian dysfunction and an inability of the eustachian tube to drain fluid from the middle ear and equalize pressure between the middle and outer ear. The results of this pathology are a negative middle ear pressure and an accumulation of fluid in the middle ear and causing middle ear infections. If left untreated, both of these conditions may cause loss of hearing, severe pain and potentially destruction of major structures of the middle ear.

Treatment of children with recurrent otitis media includes initial medical management by the administration of antibiotics. While treatment with antibiotics is effective for a majority of patients, nevertheless, a significant number of children exhibit recurrent episodes of otitis media. Treatment of recurrent cases often involves a surgical procedure referred to as myringotomy.

In a myringotomy, a small incision is made in the tympanic membrane of the eardrum and a pressure equalization or tympanostomy tube is inserted in membrane so as to provide adequate drainage and equalize pressure between the middle and outer ear with goal of reducing the likelihood of future ear infections. Tympanostomy tubes function by providing air and fluid communication between the middle ear and outer ear. The tubes may remain in place from a few months to a few years. In some patients, the tubes will fall out spontaneously within about a year of placement. In other patients, the tubes may require surgical removal.

Myringotomy is a the most common surgical procedure under general anesthesia in the pediatric population. Estimates suggest that more than one million tympanostomy tubes are placed each year, with typical patients being between about 18 months and 3 years of age at the time of the procedure. The procedure is typically performed on an out-patient basis under general anesthesia.

A wide variety of tympanostomy tubes are commercially available. Prior art tubes are typically configured as hollow cylinders having perpendicular flanges at each opening of the tube. The hollow cylinders serve to equalize air pressure on either side of the ear drum, i.e. between the middle and outer ear. The flanges of the cylinders serve to retain the tubes in the tympanic membrane. Tympanostomy tubes having a single flange are also known in the art. Prior art tube cylinders are typically about 2 to 7 millimeters in length and have diameters of about 1 to 2 millimeters.

Although a variety of prior art tubes exist, there is nevertheless room for improvement in the art. Experience has shown that prior art tubes with an internal cylinder diameter of less than 1 mm tend to clog with ear secretions. Clogging is also a function of cylinder length with longer cylinders tending to clog more easily than shorter cylinders. Even at just 2 mm in length, experience has shown that cylinder clogging remains a problem.

Flange diameters also vary significantly among currently available tubes. Flanges come in all shapes and sizes. Consequently, tubes with small diameter flanges are well-suited for some patients while other patients benefit from tubes with larger diameter flanges. As such, hospitals are required to keep tubes with a variety of flange diameters in stock to suit different patients. Prior art tubes also lack any type of valve which may assist in regulating the pressure differential and water resistance between the middle and outer ears in situations where a surgeon considers such a function desirable.

There is a need in the art for an improved tympanostomy tube design having a short cylinder length to reduce clogging and a flange design that allows the flanges to be sized to a particular patient's needs in the operating room. There is further a need for a tympanostomy tube which incorporates a valve for the regulation of pressure between the outer and middle ear, and resist intrusion of contaminated fluids into the middle ear.

SUMMARY OF THE INVENTION

The present invention meets a long-felt need in the art by providing an improved pressure equalization or tympanostomy tube which features a short cylinder length to reduce or eliminate clogging and a flange design that allows the flange to be disposed inward of the tympanic membrane to be sized by a surgeon to suit a particular patient's needs in the operating room. In one embodiment, the tympanostomy tube of the present invention also provides a cylindrical tube body having a square bore where a flap is provided across an aperture of the square bore, which functions as a valve for the regulation of pressure between a patient's middle and outer ear, and provides a resistance to the intrusion of contaminated fluid into a patient's middle ear.

The above and other advantages of the pressure equalization or tympanostomy tube of the present invention will be described in more detail below.

DETAILED DESCRIPTION OF THE PREFERRED EMBODIMENTS

The present invention will now be described more fully hereinafter with reference to the accompanying drawings, in which preferred embodiments of the invention are shown. The invention however, may be embodied in many different forms and should not be construed as being limited to the embodiments set forth herein. Rather these embodiments are provided so that this disclosure will be thorough and complete, and will fully convey the scope of the invention to those skilled in the art. Like numbers refer to like elements throughout.

Figure 1:
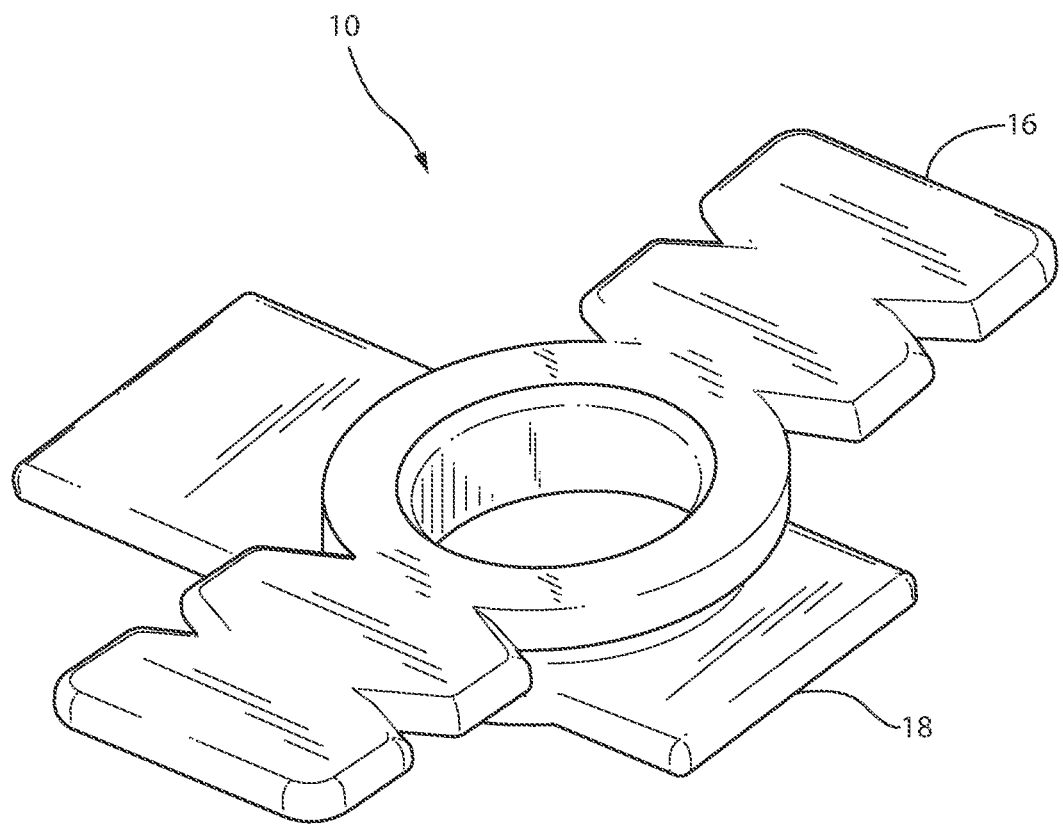
FIG. 1 is a perspective view of a first embodiment of a tympanostomy tube in accordance with the present invention.
Figure 2:
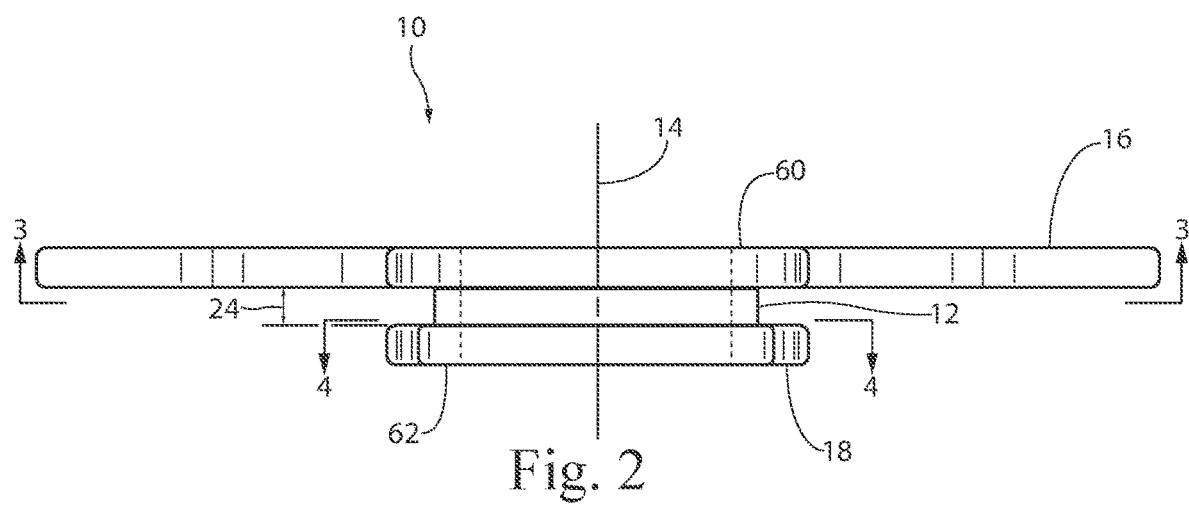
FIG. 2 is a front view of the tympanostomy tube of FIG. 1.
Figure 3:
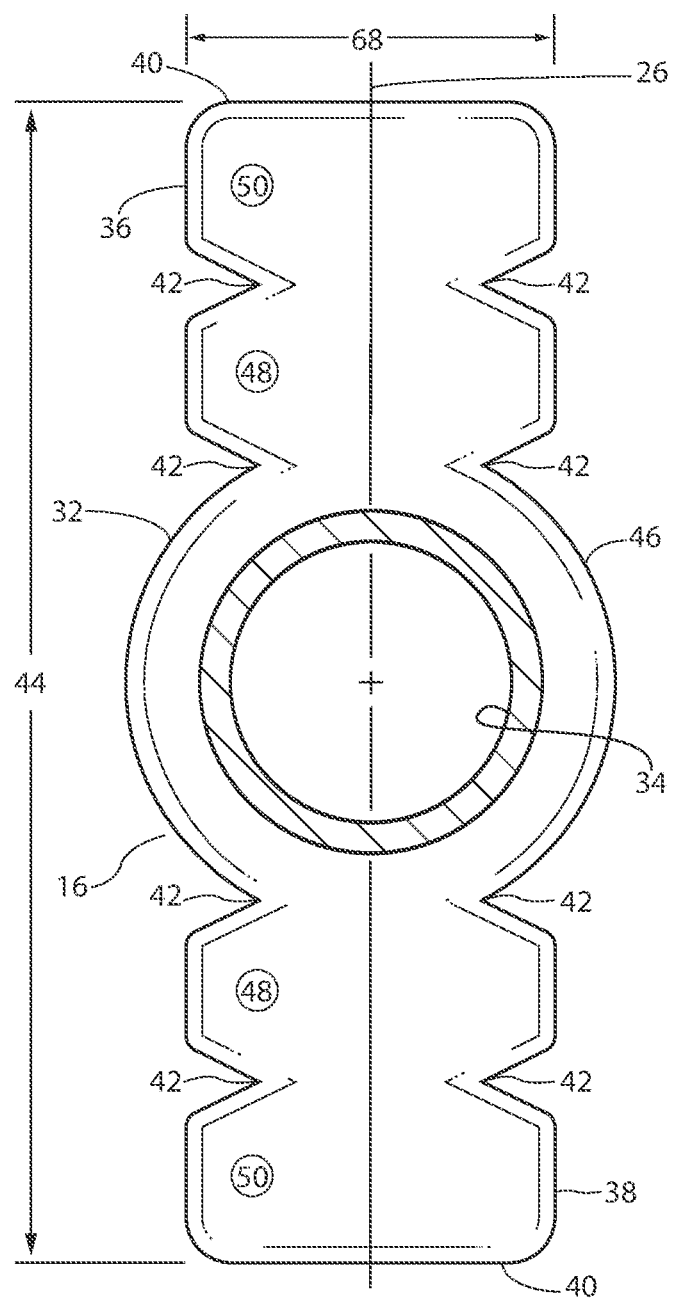
FIG. 3 is a cross-sectional view of the tympanostomy tube of FIG. 1 taken along the line 3-3 of FIG. 2.
Figure 4:
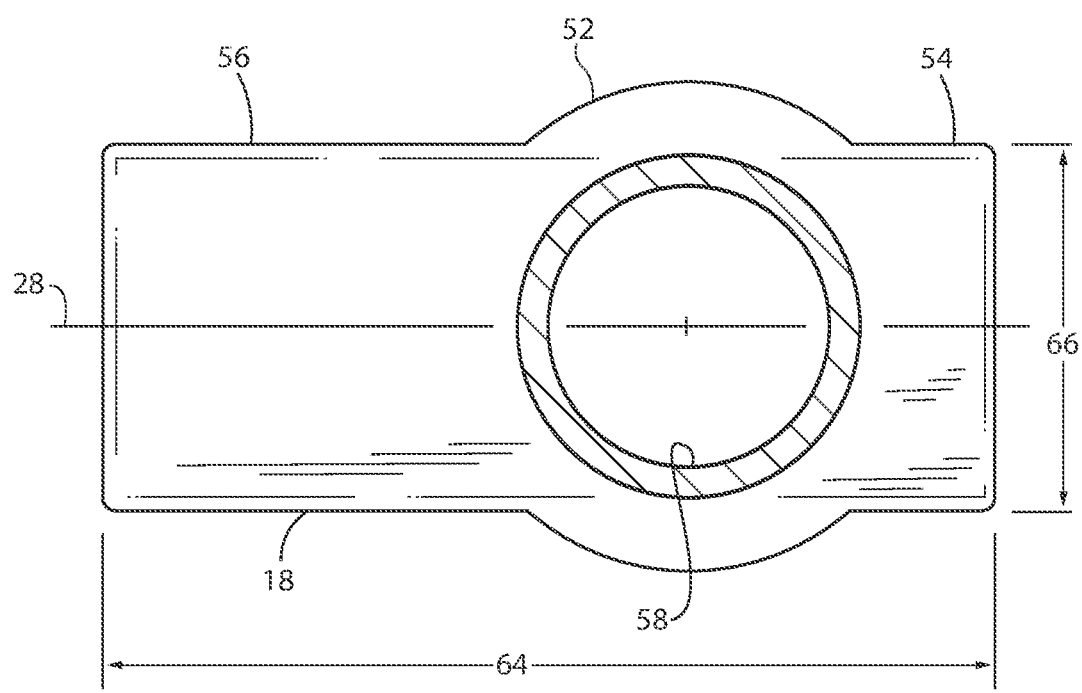
FIG. 4 is a cross-sectional view of the tympanostomy tube of FIG. 1 taken along the line 4-4 of FIG. 2.
Figure 5:
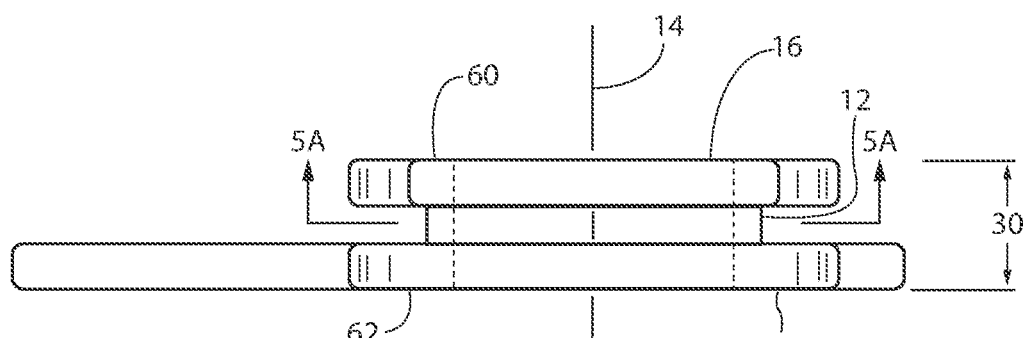
FIG. 5 is a left side view of the tympanostomy of FIG. 1.
Figure 5A:
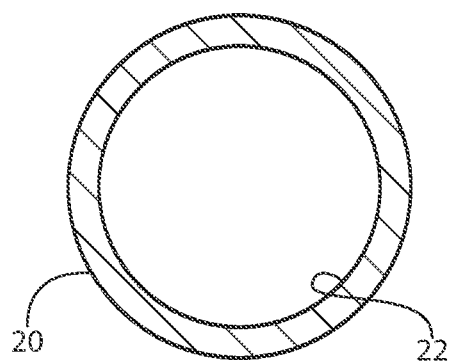
FIG. 5A is a is a cross-sectional view of the tympanostomy tube of FIG. 1 taken along the line 2A-2A of FIG. 5.
Figure 6:
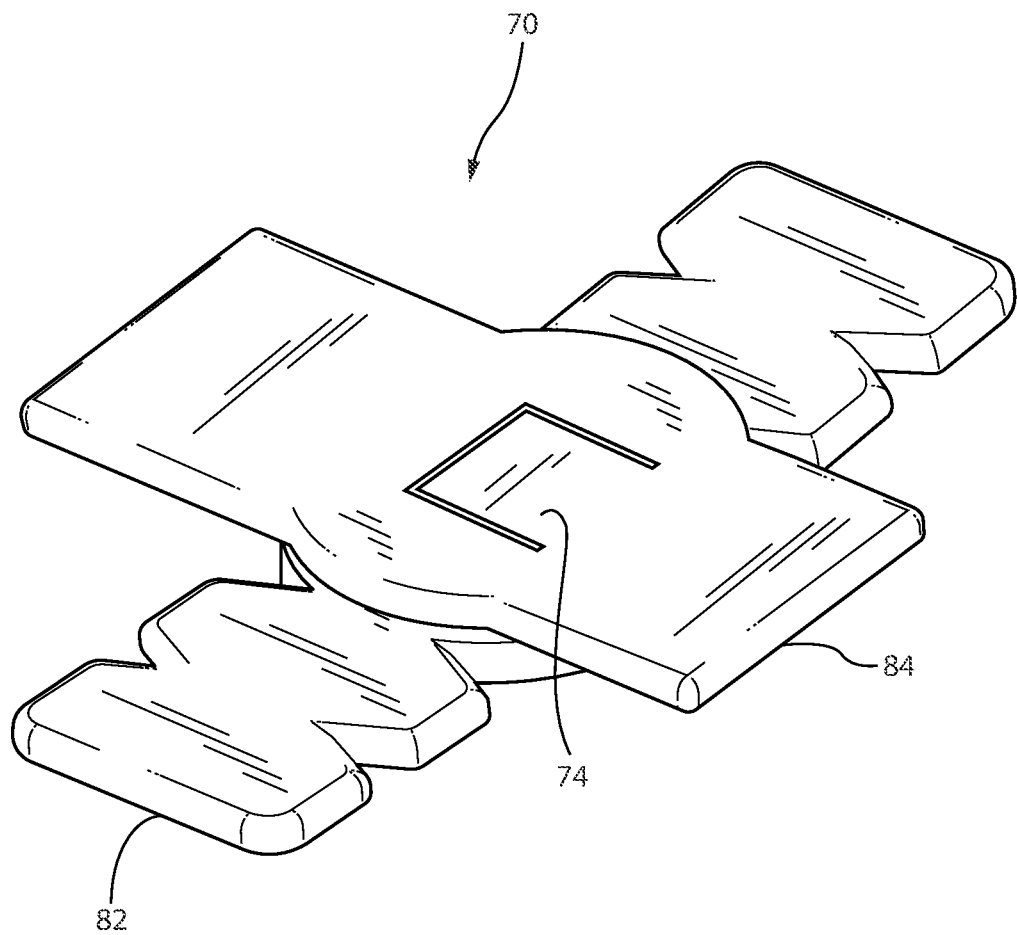
FIG. 6 is a perspective view of a second embodiment of a tympanostomy tube in accordance with the present invention.

With reference to FIGS. 1-5A and particular reference to FIGS. 2 and 5, a first exemplary embodiment of a tympanostomy tube or pressure equalization tube 10 in accordance with the present invention is depicted. The tube is suitable for placement across a tympanic membrane (not shown) of a human ear. The tympanostomy tube 10 has a first end 60 and second end 62 and an overall length or cylinder length 30 (see FIG. 5A). The tympanostomy tube 10 includes a tube body 12, a first flange 16 and a second flange 18. The tube body 12 has a longitudinal axis 14 and a hollow cylindrical cross-section having an outside diameter 20 and an inside diameter or aperture 22, and a height 24 which represents the length of the tube body 12 between the first flange 16 and second flange 18.

In the first embodiment of the tympanostomy tube 10, the overall length or cylinder length 30 of the tube 10 is within the range of about 0.90 mm to 1.50 mm, with 1.00 mm being preferred. Experience has shown that conventional prior art tubes which have a cylinder length of about 2.00 to 7.00 mm clog with ear secretions over time, with longer cylinders being more susceptible to clogging than shorter cylinders. The tympanostomy tube 10 of the present invention seeks to overcome this drawback of prior art tubes by limiting the cylinder length to about 1.00 mm.

In the first embodiment of the tympanostomy tube 10 of the present invention, the inside diameter 22 of the tube body 12 is within the range of about 1.00 to 2.00 mm, with 1.25 mm being preferred. Experience has shown that cylinders of larger inside diameter are less likely to clog than tubes of smaller inside diameter.

With continued reference to FIGS. 1-5A and particular reference to FIGS. 3 and 4, disposed perpendicular to the longitudinal axis 14 of the tube body 12 at the first end 60 of the tube body 12 is the first flange 16. The first flange 16 includes an axis of symmetry 26. Disposed perpendicular to the longitudinal axis 14 of the tube body 12 at the second end 62 of the tube body 12 is the second flange 18 which has an axis of symmetry 28. The first flange 16 and the second flange 18 are configured such that the axes of symmetry 26 and 28 of the first and second flanges 16 and 18 are perpendicular to each other, as well as to the axis of symmetry 14 of the tube body 12.

The first flange 16 comprises a central collar 46 having the aperture 22 of of the tube body 12. Extending outwardly from the central collar 46 along the axis of symmetry 26 are a first extension element 36 and a second extension element 38, where the first and second extension elements 36 and 38 are mutually opposed.

With continued reference to FIGS. 1-5A and particular reference to FIG. 3, the first and second extension elements 36 and 38 of the first flange are further divided into one or more sectors. In the exemplary embodiment depicted in FIG. 3, the first and second extension elements 36 and 38 comprise inner sectors 48 and outer sectors 50. The outer sectors 50 are separable from the inner sectors 48 by means of cutting the outer sectors 50 away from the inner sectors 48. Notches 42 are provided at the juncture between the sectors to facilitate cutting. Likewise, the inner sectors 48 are also separable from the collar 46 by means of cutting and are similarly provided with notches 42 at the juncture between the inner sectors 48 and the collar 46 to facilitate cutting.

With continued reference to FIGS. 1-5A and particular reference to FIG. 4, similar to the first flange 16, the second flange 18 also comprises a central collar 52 having the aperture 22 of the tube body 12. Extending outwardly from the central collar 52 along the axis of symmetry 28 is a first extension element 54 and a second extension element 56, where the first and second extension elements 54 and 56 are mutually opposed.

During a myringotomy, an incision is made through the tympanic membrane of a patient's ear and the first end 60 of the tympanostomy tube 10 is placed through the incision in the patient's tympanic membrane (eardrum). Consequently, the first end 60 resides in the patient's middle ear and the first flange 16 abuts an interior or inwardly facing surface of the tympanic membrane. The second end 62 of the tympanostomy tube 10 resides in the patient's outer ear with the second flange 18 abutting an exterior or outwardly facing surface of the tympanic membrane. The tympanic membrane is captured or disposed between the first and second flanges 16 and 18.

An issue that arises in performing a myringotomy, is the length of time the tympanostomy tube is expected to remain in place in a patient's eardrum. The ease with which a tympanostomy tube can be extruded or removed is dependent to a substantial degree on the size of the flange element that abuts the tympanic membrane on the interior of the middle ear, with small flanges being relatively easy to extrude or remove and larger flanges being more difficult. (In the context of this specification, "extrusion" refers to the tympanostomy tube expelled from the body by the body's own physiological processes and "removal" refers to surgical removal of a tube.) Thus, for extrusion or removal purposes, smaller flanges are to be preferred. Conversely, however, if a tube is expected to remain in place for a long period of time, for example, more than one year, a relatively large flange is required to more firmly anchor the tube in the ear as the patient's body will seek to expel the tube from the tympanic membrane over time.

In order to balance these competing demands, the tympanostomy tube 10 of the present invention equips the first and second extensions 36 and 38 of the first flange 16 with the notches 42, so as to allow a surgeon to reduce the size of the extensions by cutting across the notches or to cut the extensions away all together. This feature improves upon the prior art by providing surgeons with the ability to reduce extension size as the patient's condition warrants while in the operating room. The ability to reduce the extension size or eliminate the extensions altogether further allows a hospital reduce the number of tubes they would otherwise need to keep in stock.

With continued reference to FIGS. 1-5A, and with particular reference to FIG. 4, the second flange 18 also comprises a central collar 52 including a circular opening 58 having the inside diameter or aperture 22 of the tube body 12. Extending outwardly from the central collar 52 along the axis of symmetry 28 is a first extension element 54 and a second extension element 56, where the first and second extension elements 54 and 56 are mutually opposed.

With continued reference to FIGS. 1-5A, as discussed above, when the tympanostomy tube 10 is surgically placed, the second flange 18 resides in the patient's outer ear and abuts the outwardly facing surface of the ear's tympanic membrane. Therefore, the second flange 18 should be sufficiently large in surface area so as to prevent the tympanostomy tube 10 from falling through the tympanic membrane and into a patient's middle ear. This is accomplished by both the first and second extension elements 54 and 56. In the exemplary embodiment, the second extension element 56 is also extended in length in comparison to the first extension element 54 for the purpose of providing a tab that may be easily gripped by forceps or other surgical instruments to facilitate removal of the tube.

In the exemplary embodiment of the tympanostomy tube 10, the overall length 44 of the first flange 16 is approximately 8.00 mm and the width 68 is about 2.00 mm. Similarly, the overall length 64 of the second flange 18 is approximately 6.50 mm and the width 66 is about 2.00 mm. These dimensions are presented for reference only and are not meant to be limiting. They are provided for the purpose of presenting the approximate size of the tympanostomy tube 10. Functional tubes in accordance with the principles of the invention may be created having flanges either larger or smaller than those of the referenced exemplary embodiment.

With reference to FIG. 2, the height or length 24 of the tube body 12 between the first and second flanges 16 and 18 should be sufficient to provide space to constrain the tympanic membrane between the first and second flanges 16 and 18, without unduly harming the membrane. The tympanic membrane is quite thin, i.e. on the order of about 0.100 mm in thickness. Experience has shown that a minimum height 24 between the first flange 16 and second flange 18 of about 0.30 mm is sufficient to constrain the membrane without incurring unnecessary harm to the tissue.

Figure 7:
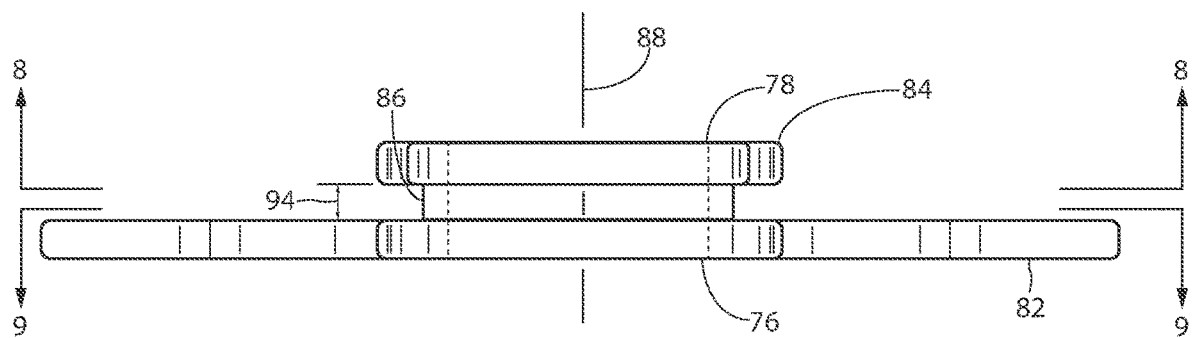
FIG. 7 is a front view of the tympanostomy tube of FIG. 6.
Figure 8:
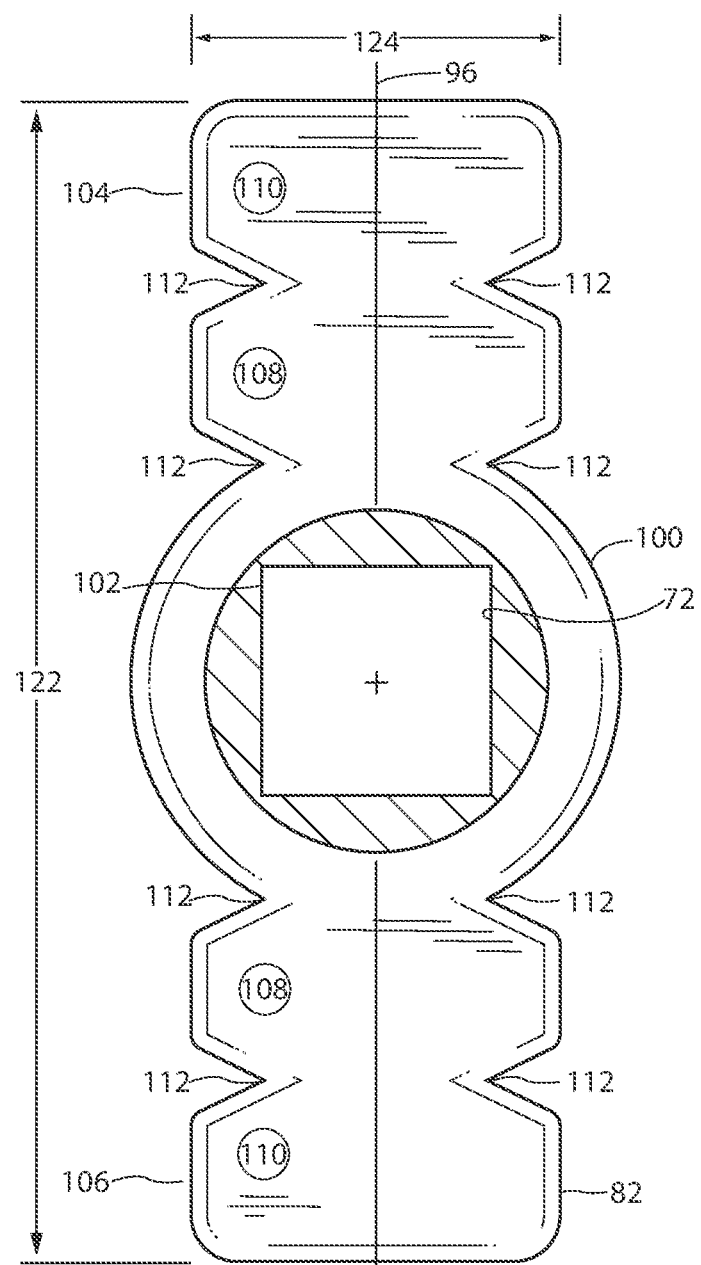
FIG. 8 is a cross-sectional view of the tympanostomy tube of FIG. 6 taken along the line 8-8 of FIG. 7.
Figure 9:
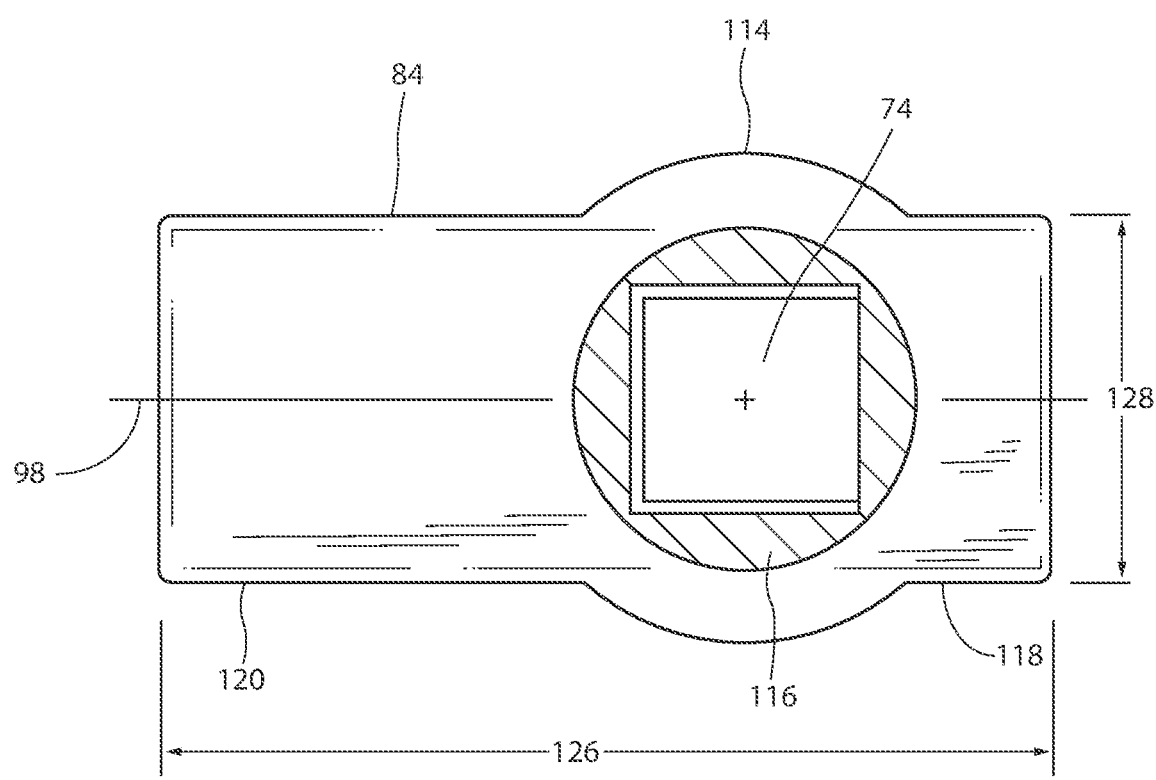
FIG. 9 is a cross-sectional view of the tympanostomy tube of FIG. 6 taken along the line 9-9 of FIG. 7.
Figure 10:
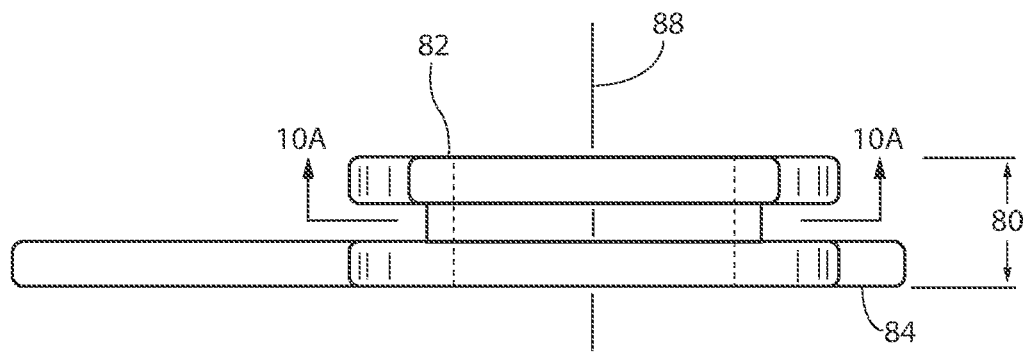
FIG. 10 is a left side view of the tympanostomy of FIG. 6.
Figure 10A:
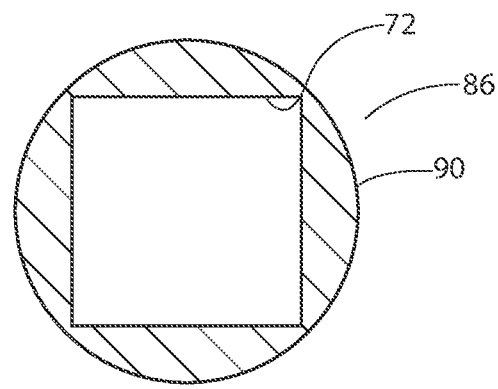
FIG. 10A is a is a cross-sectional view of the tympanostomy tube of FIG. 6 taken along the line 10A-10A of FIG. 10.

Referring now to FIGS. 6-10A, and particularly to FIGS. 7 and 10A, a second exemplary embodiment of the tympanostomy tube 70 of the present invention is presented. The second embodiment 70 differs from the first embodiment 10, in that it features a square aperture 72 (see FIGS. 8 and 10A), which allows for the inclusion of a flap valve 74 in a second flange 84, where the flap valve 74 provides the ability to control pressure between the middle and outer ear.

With continued reference to FIGS. 6-10A, and with particular reference to FIGS. 7 and 10A, the second embodiment of the tympanostomy tube 70 has a first end 76 and a second end 78 and an overall length or cylinder length 80 (see FIG. 10). The second embodiment of the tube 70 includes a tube body 86, a first flange 82 and the second flange 84. The tube body 86 has a longitudinal axis 88 and a cylindrical cross-section 90 having a square aperture 72, i.e. the tube body features a square bore. The tube body has a length 94, which represents the length of the tube body 86 between the first and second flanges 82 and 84.

Similar to the first embodiment of the tympanostomy tube 10, in the second embodiment of the tympanostomy tube 70, the overall length or cylinder length 80 of the tympanostomy tube 70 is in the range of about 0.90 mm to 1.50 mm, with 1.00 mm being preferred. Prior art tympanostomy tubes having a cylinder length of about 2.00 to 7.00 mm tend to clog with ear secretions over time. Clogging is function of cylinder length and cylinder inside diameter. Like the first embodiment of the tympanostomy tube 10, the second embodiment of the tympanostomy tube 70 seeks to prevent tube clogging by limiting the overall length or cylinder length 80 of the tube body 86 to about 1.00 mm.

In the second embodiment of the tympanostomy tube 70, the square aperture 72 of the tube body 86 is within the range of about 1.00 to 2.20 mm square, i.e. per side, with 2.00 mm square being preferred.

With continued reference to FIGS. 6-10A, and with particular reference to FIGS. 8 and 9, the first and second flanges of the first embodiment 10 and second embodiment 70 of the tympanostomy tube of the present invention function similarly. In the second embodiment 70, disposed perpendicular to the longitudinal axis 88 of the tube body 86 at a first end 76 of the tube body 86 is the first flange 82 which includes an axis of symmetry 96. Disposed perpendicular to the longitudinal axis 88 of the tube body 86 at the second end 78 of the tube body is the second flange 84 having an axis of symmetry 98. The first flange 82 and the second flange 84 are configured such that the axes of symmetry 96 and 98 are perpendicular to each other, as well as to the axis of symmetry 88 of the tube body 86.

With continued reference to FIGS. 6-10A, and with particular reference to FIG. 8, the first flange 82 of the second embodiment 70 comprises a central collar 100 featuring the square aperture or opening 72 of the bore of the tube body 86. Extending outwardly from the central collar 100 along the axis of symmetry 96 are a first extension element 104 and a second extension element 106, where the first and second extension elements 104 and 106 are mutually opposed.

The first and second extension elements 104 and 106 of the first flange 82 are further divided into one or more sectors. In the second embodiment 70 depicted in FIG. 8, the first and second extension elements 104 and 106 comprise inner sectors 108 and outer sectors 110. The outer sectors 110 are separable from the inner sectors 108 by means of cutting the outer sectors 110 away from the inner sectors 108. Notches 112 are provided at the juncture between the sectors to facilitate cutting. Likewise, the inner sectors 108 are separable from the collar 100 by means of cutting and are similarly provided with notches 112 at the juncture between the inner sectors 108 and the collar 100 to facilitate cutting.

With continued reference to FIGS. 6-10A, and with particular reference to FIG. 9, similar to the first flange 82 of the second embodiment to the tympanostomy tube 70, the second flange 84 also comprises a central collar 114 featuring the square aperture or opening 72 of the tube body 86. Extending outwardly from the central collar 114 along the axis of symmetry 98 is a first extension element 118 and a second extension element 120, where the first and second extension elements 118 and 120 are mutually opposed.

During a myringotomy, the first flange 82 of the tympanostomy tube 70 is placed through the incision in the patient's tympanic membrane. Consequently, the first flange 82 resides in the patient's middle ear and abuts an interior or inwardly facing surface of the tympanic membrane. The second flange 84 resides in the patient's outer ear abutting an exterior or outwardly facing surface of the tympanic membrane. The tympanic membrane is captured or disposed between the first and second flanges 82 and 84.

As with the first embodiment of the of the tympanostomy tube 10, with the second embodiment of the tube 70, the first and second extensions 104 and 106 of the first flange 82 may be cut to a desired size by a surgeon prior to or while performing a myringotomy procedure and notches 112 in the extensions are provided to facilitate sizing of the extensions. Also, similar the first embodiment of the tube 10, in the second embodiment of the tube 70, the second flange 84 serves to prevent the tube 70 from falling into a patient's middle ear after placement and is similarly equipped with the elongated second extension element 120 for the purpose of providing a tab that may be easily grasped by forceps or other suitable surgical tool to facilitate removal of the tube.

Similar to the first embodiment of the tympanostomy tube 10, in the second embodiment of the tube 70, the overall length 122 of the first flange 82 is approximately 8.00 mm and the width 124 is approximately 2.00 mm. Similarly, the overall length 126 of the second flange 84 is approximately 6.50 mm and the width 128 is approximately 2.00 mm. The above dimensions are presented for reference only and are not meant to be limiting.

Where a square aperture tympanostomy tube may be desired, the second embodiment 70 of the present invention tube may be fabricated without the flap valve 74, or, alternatively, the flap valve 74 may be cut away prior to insertion.

The tympanostomy tubes of the present invention may be made from a variety of biocompatible materials including biologically inert plastics, ceramics and metals, with medical grade silicone being preferred. Any such material approved by applicable regulatory agencies for use in the human body is suitable. Flexible plastic materials having a durometer within the range of about 20 to about 60, with 50 durometer being presently preferred, are particularly well-suited to this application.

It will be appreciated that a new tympanostomy tube design that overcomes the clogging associated with prior art tubes, allows for surgeon sizing of the tube extension elements, and provides, in one embodiment, a valve to regulate pressure between the middle and outer ear and resists contaminated fluid into the middle ear, has been presented. While the present invention has been described with regards to particular embodiments, it is recognized that additional variations of the present invention may be devised without departing from the inventive concept.

What is claimed is:

1. A tympanostomy tube for placement across a myringotomy incision in a tympanic membrane of an ear, comprising:
    a cylindrical body having a first end and a second end with a square bore therebetween, the first end intended to be disposed through the myringotomy incision inwardly of the tympanic membrane and the second end intended to be disposed outwardly of the tympanic membrane;
    wherein the square bore includes a bidirectional flap valve;
    wherein the first end includes a central collar having mutually opposed extension elements, each extension element comprising at least two adjacent sectors, each adjacent sector partially separated by a pair of mutually opposed notches;
    wherein each extension element of the first end may be reduced in size by removing an adjacent sector by means of cutting across the pair of mutually opposed notches;
    wherein the second end includes a central collar having mutually opposed extension elements; and
    the mutually opposed extension elements of the second end are graspable by a surgical tool.

2. The tympanostomy tube for placement across a myringotomy incision in a tympanic membrane of an ear, of claim 1, wherein the mutually opposed extension elements of the first end and the second end are perpendicular to the cylindrical body.

3. The tympanostomy tube for placement across a myringotomy incision in a tympanic membrane of an ear, of claim 1, wherein the mutually opposed extension elements of the first end and the second end are perpendicular to the cylindrical body and are perpendicular to each other.

4. The tympanostomy tube for placement across a myringotomy incision in a tympanic membrane in an ear of claim 1, wherein the tympanostomy tube has a maximum length within the range of 0.90 mm to 1.50 mm.

5. The tympanostomy tube for placement across a myringotomy incision in a tympanic membrane in an ear of claim 1, wherein the tympanostomy tube has a maximum length of 1.00 mm.

6. The tympanostomy tube for placement across a myringotomy incision in a tympanic membrane in an ear of claim 1, wherein the square bore has an interior dimension of 1.50 mm to 2.00 mm square.

7. The tympanostomy tube for placement across a myringotomy incision in a tympanic membrane in an ear of claim 1, wherein the square bore has an interior dimension of 2.00 mm square.

8. The tympanostomy tube for placement across a myringotomy incision in a tympanic membrane of an ear, of claim 1, wherein the mutually opposed extension elements are rectangular.

9. A tympanostomy tube for placement across a myringotomy incision in a tympanic membrane in an ear, comprising:
    a cylindrical body having a first end and a second end with a cylindrical bore therebetween, the first end intended to be disposed through the myringotomy incision inwardly of the tympanic membrane and the second end intended to be disposed outwardly of the tympanic membrane;
    wherein the first end includes a central collar having mutually opposed extension elements, each extension element comprising at least two adjacent sectors, each adjacent sector partially separated by a pair of mutually opposed notches;
    wherein each extension element of the first end may be reduced in size by removing an adjacent sector by means of cutting across the pair of mutually opposed notches;
    wherein the second end includes a central collar having mutually opposed extension elements; and
    the mutually opposed extension elements of the second end are graspable by a surgical tool.

10. The tympanostomy tube for placement across a myringotomy incision in a tympanic membrane of an ear, of claim 9, wherein the mutually opposed extension elements of the first end and the second end are perpendicular to the cylindrical body.

11. The tympanostomy tube for placement across a myringotomy incision in a tympanic membrane of an ear, of claim 9, wherein the mutually opposed extension elements of the first end and the second end are perpendicular to the cylindrical body and are perpendicular to each other.

12. The tympanostomy tube for placement across a myringotomy incision in a tympanic membrane in an ear of claim 11, wherein the tympanostomy tube has a maximum length within the range of 0.90 mm to 1.50 mm.

13. The tympanostomy tube for placement across a myringotomy incision in a tympanic membrane in an ear of claim 11, wherein an inside diameter of the cylindrical bore is 2.00 mm.

14. The tympanostomy tube for placement across a myringotomy incision in a tympanic membrane in an ear of claim 9, wherein the tympanostomy tube has a maximum length of 1.00 mm.

15. The tympanostomy tube for placement across a myringotomy incision in a tympanic membrane in an ear of claim 9, wherein an inside diameter of the cylindrical bore is within the range of 1.00 mm to 2.00 mm.

16. The tympanostomy tube for placement across a myringotomy incision in a tympanic membrane of an ear, of claim 9, wherein the mutually opposed extension elements are rectangular.

17. A tympanostomy tube for placement across a myringotomy incision in a tympanic membrane of an ear, comprising:
   a cylindrical body having a first end and a second end with a square bore therebetween, the first end intended to be disposed through the myringotomy incision inwardly of the tympanic membrane and the second end intended to be disposed outwardly of the tympanic membrane;
   wherein the first end includes a central collar having mutually opposed extension elements, each extension element comprising at least two adjacent sectors, each adjacent sector partially separated by a pair of mutually opposed notches;
   wherein the second end includes a central collar having mutually opposed extension elements; and
   the mutually opposed extension elements of the second end are graspable by a surgical tool.

18. The tympanostomy tube for placement across a myringotomy incision in a tympanic membrane in an ear of claim 17, wherein the tympanostomy tube has a maximum length within the range of 0.90 mm to 1.50 mm.

* * * * *